(12) United States Patent
Ehlert et al.

(10) Patent No.: US 9,463,150 B2
(45) Date of Patent: *Oct. 11, 2016

(54) AGENT FOR COLORING AND/OR LIGHTENING KERATINIC FIBERS WITHOUT AMMONIA ODOR

(71) Applicant: Henkel AG & Co. KGaA, Duesseldorf (DE)

(72) Inventors: Manuela Ehlert, Leverkusen (DE); Irmgard Bender, Duesseldorf (DE); Mechtild Grunwald, Langenfeld (DE); Constanze Neuba, Grevenbroich (DE); Norbert Schettiger, Hilden (DE); Sabine Babiel, Moers (DE); Anja Reichert, Duesseldorf (DE); Daniela Kessler-Becker, Leverkusen (DE); Astrid Kleen-Fehres, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/576,522

(22) Filed: Dec. 19, 2014

(65) Prior Publication Data

US 2016/0175234 A1    Jun. 23, 2016

(51) Int. Cl.
| | | |
|---|---|---|
| *A61Q 5/10* | (2006.01) | |
| *A61K 8/86* | (2006.01) | |
| *A61K 8/19* | (2006.01) | |
| *A61K 8/22* | (2006.01) | |
| *A61K 8/34* | (2006.01) | |
| *A61K 8/41* | (2006.01) | |

(52) U.S. Cl.
CPC . *A61K 8/86* (2013.01); *A61K 8/19* (2013.01); *A61K 8/22* (2013.01); *A61K 8/342* (2013.01); *A61K 8/41* (2013.01); *A61Q 5/10* (2013.01); *A61K 2800/5922* (2013.01); *A61K 2800/75* (2013.01); *A61K 2800/882* (2013.01); *A61K 2800/884* (2013.01)

(58) Field of Classification Search
CPC ............ A61Q 5/10; A61K 8/19; A61K 8/22; A61K 8/342; A61K 8/41; A61K 8/86
USPC ............................................................. 8/405
See application file for complete search history.

(56) References Cited

U.S. PATENT DOCUMENTS

| | | | | |
|---|---|---|---|---|
| 8,845,758 B2* | 9/2014 | Neuba | ...................... | A61K 8/22 8/405 |
| 8,882,854 B2* | 11/2014 | Neuba | ...................... | A61K 8/34 8/405 |
| 2004/0103488 A1* | 6/2004 | Yamashita | ............. | A61K 8/046 8/406 |
| 2012/0048288 A1* | 3/2012 | Reichert | ................ | A61K 8/442 132/208 |

FOREIGN PATENT DOCUMENTS

| | | |
|---|---|---|
| JP | 2003-040750 A | 2/2003 |
| JP | 2007-191459 A | 8/2007 |
| WO | 2005/110499 A1 | 11/2005 |
| WO | 2006/060565 A2 | 6/2006 |
| WO | 2006/060570 A2 | 6/2006 |

* cited by examiner

*Primary Examiner* — Eisa Elhilo
(74) *Attorney, Agent, or Firm* — David K. Benson

(57) ABSTRACT

An agent for coloring and/or lightening keratinic fibers, in particular human hair, includes:
   (a) ammonia in a quantity of 0.40 to 3.0 wt.-%, preferably of 0.50 to 2.4 wt.-%, more preferably of 0.60 to 2.0 wt.-% and especially preferred of 0.62 to 1.75 wt.-%, based on the weight of the agent,
   (b) one or more alkanolamines from the group of monoethanolamine, 2-amino-2-methylpropanol, and triethanolamine,
   (c) one or more ethoxylated fatty alcohols having a degree of ethoxylation from 80 to 120,
   (d) cetyl alcohol and stearyl alcohol in a total quantity of 4 to 8 wt-%, based on the weight of the agent,
   (e) one or more ethoxylated fatty alcohols having a degree of ethoxylation of 30.

11 Claims, No Drawings

AGENT FOR COLORING AND/OR LIGHTENING KERATINIC FIBERS WITHOUT AMMONIA ODOR

FIELD OF THE INVENTION

The present invention generally relates to agents for coloring and/or lightening keratinic fibers, in particular human hair. A further field of the present invention is that of ready-to-use agents that are produced by mixing one of the aforesaid agents with a further separate component including water and hydrogen peroxide.

BACKGROUND OF THE INVENTION

One skilled in the art knows of a variety of coloring systems, depending on the required color result, for making available color-changing cosmetic agents, in particular for keratinic fibers such as e.g. human hair. For permanent, intense color results having corresponding fastness properties, so-called "oxidation" coloring agents are used. Such coloring agents usually include oxidation dye precursors called "developer components" and "coupler components" that, under the influence of oxidizing agents such as hydrogen peroxide, form the actual dyes with one another. Oxidizing coloring agents are notable for outstanding, long-lasting color results. In addition to coloring, lightening of one's own hair color, and often hair-bleaching, is a very special desire of many consumers. For this, the natural or artificial dyes coloring the fibers are usually decolorized oxidatively using corresponding oxidizing agents, for example hydrogen peroxide.

In order to provide satisfactory coloring and lightening performance, oxidative coloring agents and/or lightening agents generally require an alkaline pH during utilization; optimum results are achieved in particular at pH values between 8.5 and 10.5.

Until the present time, ammonia has been the alkalizing agent of choice for establishing these pH values. Not only can ammonia be used to establish the pH range necessary for dye formation, but ammonia also ensures swelling of the hair to a greater extent than all other known alkalizing agents. At the same time, ammonia acts as a penetration adjuvant.

The applications-engineering advantages associated with the use of ammonia are so numerous that despite its unpleasant, pungent odor, ammonia is used in a large number of commercial oxidative coloring agents.

Extensive efforts to reduce the ammonia odor are already known from the literature. A variety of possibilities exist for minimizing the odor: as a first possibility, the literature recites varying the alkalizing agent and thus partly or entirely replacing ammonia with odorless alternatives.

A plurality of formulations that employ a mixture of ammonia and monoethanolamine, or exclusively monoethanolamine, as an alkalizing agent already exist in the literature. Reducing the ammonia content often results, however, in poorer penetration of the dyes into the hair, which can be reflected especially in poorer gray coverage and poorer washing fastness.

Although complete or partial replacement of ammonia with alternative alkalizing agents has advantageous effects in terms of minimizing the odor of the coloring and/or lightening agents, it is associated with disadvantages in terms of the fastness properties of the color results obtained with the coloring and/or lightening agents. If a corresponding replacement of the alkalizing agent is made, the resulting losses in terms of coloring performance must be compensated for by optimizing the formulation.

WO 2006060570 and WO 2006060565 propose the use of carbonates or carbonate sources as alkalizing agents in order to furnish oxidative coloring agents with little odor impact. It is likewise known in the literature, however, that carbonates in combination with oxidizing agents can damage the hair to a greater extent. The additional damage to the hair brought about by carbonates may not be much of a problem when utilizing the coloring agent on untreated or undamaged hair, but in the case of persons who regularly color or bleach their hair it can add up to serious cumulative damage. If more intense lightening and/or regular coloring is desired, the use of carbonates therefore once again does not represent a feasible alternative.

A second possibility, in principle, for reducing ammonia odor consists in the addition of special perfume substances that are intended to mask the ammonia odor. This approach is taken, for example, in WO 2005/110499. Perfume substances can be unstable under alkaline storage conditions, however, so that the risk exists that the scents may become degraded or structurally modified during storage, which is also reflected in an unpredictable change in odor. Because corresponding changes often become perceptible only after several months or even years, the employment of new or unknown perfumes is considered problematic.

A third general possibility for reducing ammonia odor consists in optimizing the formulation. The idea here is to select the carrier constituents of the formulation in such a way that they ensure optimum retention of ammonia in the formulation, and in that manner minimize its odor. It is once again known, however, that the formulation, the fatty substances included in it, its emulsifier agents and surfactants, and its viscosity have a substantial influence on coloring performance. When the formulation is modified, a deterioration in coloring performance must therefore in all cases be avoided.

For example, JP 2007191459 proposes the use of cationic surfactants, phosphate esters, and aliphatic alcohols in order to reduce ammonia odor in hair coloring agents.

JP 2003040750 discloses that the ammonia odor in hair-bleaching agents is particularly low when at least 5% of a crystalline component is added to the agents.

Although the literature proposes several methods for reducing the odor impact caused by ammonia, there is nevertheless no known possibility for completely suppressing ammonia odor.

It is therefore desirable to make available almost odorless agents for oxidative coloring and/or lightening of hair. To meet the performance requirements imposed on these agents, they are to include ammonia, but the ammonia odor is to be substantially completely masked. In particular, the complete masking of the ammonia odor is intended to persist over a long period of time, so that even after storage of the agents (in a closed vessel) for several weeks, optimally for several months, no ammonia odor is perceptible. At the same time, the agents are to exhibit no loss in terms of their coloring performance, in particular in terms of their gray coverage and their washing fastness. In addition, utilization of the agent is not to be associated with greater hair damage.

It is also desirable to successfully mask the ammonia odor for the entire duration of use, the intention being that even after a maximum of two hours of contact, no ammonia odor—and moreover also no other chemical odor—is to be perceptible.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

An agent for coloring and/or lightening keratinic fibers, in particular human hair, includes: ammonia in a quantity of 0.40 to 3.0 wt.-%, preferably of 0.50 to 2.4 wt.-%, more preferably of 0.60 to 2.0 wt.-% and especially preferred of 0.62 to 1.75 wt.-%, based on the weight of the agent; one or more alkanolamines from the group of monoethanolamine, 2-amino-2-methylpropanol, and triethanolamine; one or more ethoxylated fatty alcohols having a degree of ethoxylation from 80 to 120; cetyl alcohol and stearyl alcohol in a total quantity of 4 to 8 wt-%, based on the weight of the agent; and one or more ethoxylated fatty alcohols having a degree of ethoxylation of 30.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

In the course of the work leading to this invention it has emerged, surprisingly, that it is possible for the ammonia included in agents for coloring and/or lightening to be entirely masked in terms of olfaction, particularly for olfactory perception thereof to be completely prevented, when a special combination of different alkalizing agents is employed and when these various alkalizing agents are simultaneously combined with a mixture of specially ethoxylated fatty alcohols and cetearyl alcohol.

A first subject of the present invention is therefore an agent for coloring and/or lightening keratinic fibers, in particular human hair, including:
  (a) ammonia in a quantity of 0.40 to 3.0 wt.-%, preferably of 0.50 to 2.4 wt.-%, more preferably of 0.60 to 2.0 wt.-% and especially preferred of 0.62 to 1.75 wt.-%, based on the weight of the agent,
  (b) one or more alkanolamines from the group of monoethanolamine, 2-amino-2-methylpropanol, and triethanolamine,
  (c) one or more ethoxylated fatty alcohols having a degree of ethoxylation from 80 to 120,
  (d) cetyl alcohol and stearyl alcohol in a total quantity of 4 to 8 wt-%, based on the weight of the agent,
  (e) one or more ethoxylated fatty alcohols having a degree of ethoxylation of 30.

"Keratin-containing fibers" are understood in principle as all animal hair, e.g. wool, horsehair, angora wool, furs, feathers, and products or textiles produced therefrom. Preferably, however, the keratinic fibers are human hairs.

The term "agents for coloring and/or lightening" keratin fibers that is used according to the present invention is understood to mean agents for oxidative coloring of hair and agents for oxidative lightening or bleaching of hair.

In order to produce color, oxidative coloring agents include oxidation dye precursors, so-called "developers" and "coupler components." Developers and couplers diffuse separately into the keratin fibers and, under the influence of ammonia as an alkalizing agent and an oxidizing agent (usually hydrogen peroxide), react chemically with one another to form the actual dyes. Depending on the quantity of oxidizing agent employed, the keratin fibers are simultaneously lightened to a greater or less extent during coloring, since the oxidizing agent not only initiates the dye-forming process of the developers and couplers, but also oxidatively destroys the hair's own pigments (melanins). Depending on the quantities of oxidation dye precursors and oxidizing agent that are used, the oxidative coloring process can therefore involve predominantly coloring (with a high dye proportion) or predominantly lightening (with a high proportion of oxidizing agent). In the latter case, the oxidation dye precursors are employed principally to tint the lightening result.

Agents for oxidative lightening or bleaching of hair often include hydrogen peroxide as the only oxidizing agent in order to achieve a moderate bleaching effect, but if there is a desire for more intense hair-bleaching performance they can also include oxidizing agent mixtures. In the latter case hydrogen peroxide is usually employed in combination with persulfates such as potassium persulfate, sodium persulfate, and/or ammonium persulfate. Agents for oxidative lightening or bleaching can likewise additionally include oxidation dye precursors, but the focus of these agents is on lightening of fibers.

In a preferred embodiment, the agents according to the present invention are agents for oxidative coloring of hair.

The agents according to the present invention include the constituents essential to the invention in a cosmetic carrier, preferably in a suitable aqueous, alcoholic, or aqueous alcoholic carrier. For hair-coloring purposes such carriers are, for example, creams, emulsions, gels, or also surfactant-including foaming solutions, for example shampoos, foam aerosols, foam formulations, or other preparations that are suitable for utilization on the hair.

As a first essential formulation constituent (a), the agents according to the present invention for coloring and/or lightening keratin fibers include ammonia in a quantity of 0.40 to 3.0 wt.-%, preferably of 0.50 to 2.4 wt.-%, more preferably of 0.60 to 2.0 wt.-% and especially preferred of 0.62 to 1.75 wt.-%, based on the weight of the agent.

Ammonia is employed preferably in the form of its aqueous solution. Corresponding aqueous ammonia solutions can be 10- to 35-percent solutions (calculated in wt %; 100 g aqueous ammonia solution accordingly includes 10 to 35 g ammonia). Ammonia is employed preferably in the form of a 20 to 30 wt % solution, particularly preferably in the form of a 25 wt % solution.

In order for the agents according to the present invention to conform to the requirements profile imposed upon them in terms of their color intensity and their fastness properties, it is not possible to dispense with the use of ammonia. It has emerged, however, that ammonia can be completely masked olfactorily if it is included in specific quantity ranges in the agents according to the present invention. Complete masking by means of the further ingredients (c), (d) and (e) that are essential to the invention and are likewise included in the agent according to the present invention is possible when the inventive agents include ammonia (a) in a quantity from 0.40 to 3.0 wt.-%, preferably of 0.50 to 2.4 wt.-%, more preferably of 0.60 to 2.0 wt.-% and especially preferred of 0.62 to 1.75 wt.-%, based on the weight of the agent.

In a more preferred embodiment, an agent for coloring and/or lightening keratinic fibers is therefore characterized in that it includes ammonia (a) in a quantity from 0.50 to 2.5 wt %, more preferably from 0.60 to 2.0 wt %, and particularly preferably from 0.62 to 1.75 wt %, based on the weight of the agent.

The aforementioned preferred and particularly preferred quantitative indications of ammonia (a) assume pure ammonia as a basis for calculation. If 0.62 to 1.75 wt % ammonia (a) is therefore employed very particularly preferably in the inventive agent, this corresponds to the utilization of a quantity from 2.48 g to 7.0 g of a 25 wt % ammonia solution in the inventive coloring agent.

When ammonia in the above-described quantity ranges is furthermore combined with the alkalizing agent (b), color results with high color intensity and outstanding fastness properties can then be generated with the corresponding agents according to the present invention. Surprisingly, with the use of a combination of the constituents (a) to (e) that are essential to the invention, not only are losses in color intensity avoided, but moreover the color results produced with these agents in fact exhibit improved gray coverage and improved washing fastness.

The agents according to the present invention for coloring and/or lightening keratinic fibers include, as a second constituent (b) essential to the invention, one or more alkanolamines from the group of monoethanolamine (2-aminoethanol, formula A), 2-amino-2-methylpropanol (2-amino-2-methylpropan-1-ol, formula B), and triethanolamine (formula C).

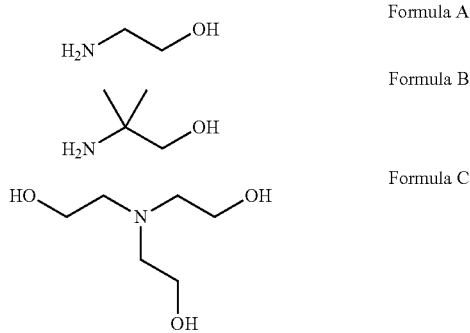

In order to achieve maximum odor masking and in order to optimize fastness properties, the alkanolamine(s) is/are also preferably employed in special quantitative ranges. Complete masking of the ammonia odor, and at the same time particularly good washing fastness values, are achieved when the alkanolamines (b) are included in a total quantity from 0.4 to 13 wt %, preferably from 1.0 to 8.0 wt %, more preferably from 1.54 to 5.0 wt %, and particularly preferably from 1.6 to 3.2 wt %, based on the weight of the agent.

In a further preferred embodiment, an agent for coloring and/or lightening keratinic fibers is therefore characterized in that it includes one or more alkanolamines (b) from the group of monoethanolamine, 2-amino-2-methylpropanol, and triethanolamine in a total quantity from 0.4 to 13 wt %, preferably from 1.0 to 8.0 wt %, more preferably from 1.54 to 5.0 wt %, and particularly preferably from 1.6 to 3.2 wt %, based on the weight of the agent.

A preferred agent according to the present invention includes, all quantity indications being based on the weight of the agent,
(a) 0.40 to 3.0 wt % ammonia,
(b) 0.4 to 13.0 wt % monoethanolamine,
(c) in a total quantity of 0.2 to 3.0 wt.-%, preferably of 0.4 bis 2.4 wt.-%, further preferred of 0.6 to 1.8 wt.-% and especially preferred of 0.8 to 1.6 wt.-%, one or more ethoxylated fatty alcohols having a degree of ethoxylation from 80 to 120,
(d) cetyl alcohol and stearyl alcohol in a total quantity of 4 to 8 wt.-%, and
(e) in a total quantity of 4 to 8 wt.-% one or more ethoxylated fatty alcohols having a degree of ethoxylation of 30.

As a third formulation constituent (c) essential to the invention, the agents according to the present invention include one or more ethoxylated fatty alcohols having a degree of ethoxylation from 80 to 120.

"Fatty alcohols" are to be understood according to the present invention as saturated or unsaturated, unbranched or branched $C_8$ to $C_{28}$ alkyl groups with hydroxy substitution. Unsaturated fatty alcohols can be mono- or polyunsaturated. In the case of an unsaturated fatty alcohol, its carbon-carbon double bond(s) can exhibit the cis- or trans-configuration.

Preferred fatty alcohols are octan-1-ol (octyl alcohol, capryl alcohol), decan-1-ol (decyl alcohol, caprinyl alcohol), dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenyl alcohol), eicosan-1-ol (eicosyl alcohol, arachyl alcohol), (9Z)-eicos-9-en-1-ol (gadoleyl alcohol), (5Z,8Z,11Z,14Z)-eicosa-5,8,11,14-tetraen-1-ol (arachidonyl alcohol), docosan-1-ol (docosyl alcohol, behenyl alcohol), (13E)-docosen-1-ol (brassidyl alcohol), and (13Z)-docos-13-en-1-ol (erucyl alcohol). Within this group in turn, hexadecan-1-ol (hexadecyl alcohol, cetyl alcohol, palmityl alcohol) and octadecan-1-ol (octadecyl alcohol, stearyl alcohol) are very particularly preferred fatty alcohols.

In order to constitute the constituent (c) essential to the present invention, these fatty alcohols are ethoxylated with a degree of ethoxylation from 80 to 120.

"Ethoxylation" (also "oxyethylation") is understood as the reaction of fatty alcohols with ethylene oxide (EU). The insertion of from 80 to 120 groups of the —$CH_2$—$CH_2$—O— type per fatty alcohol molecule yields linear polyethers that carry at one end of the chain a hydroxy group and at the other end of the chain the $C_8$ to $C_{28}$ alkyl group of the fatty alcohol.

Preferred ethoxylated fatty alcohols (c) have a degree of ethoxylation from 90 to 110. It is very particularly preferred if ethoxylated fatty alcohols (c) having a degree of ethoxylation of 100 are employed.

In a further very particularly preferred embodiment, an agent for coloring and/or lightening keratinic fibers is characterized in that it includes as (an) ethoxylated fatty alcohol(s) (c) having a degree of ethoxylation from 80 to 120 one or more compounds of formula (I)

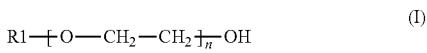

in which R1 denotes a saturated or unsaturated, unbranched or branched $C_8$ to $C_{24}$ alkyl group, preferably a saturated, unbranched $C_{16}$ or $C_{18}$ alkyl group, and n denotes an integer from 80 to 120, preferably an integer from 90 to 110, and particularly preferably the number 100.

In the course of the work leading to this invention it has emerged that, surprisingly, the degree of ethoxylation of the ethoxylated fatty alcohol (c) substantially influences the ability of the agent to reduce ammonia odor. For this reason, it is particularly preferred if one or more ethoxylated fatty alcohols having a very specific degree of ethoxylation are employed as (an) ethoxylated fatty alcohol(s).

A particularly advantageous and thus explicitly very particularly preferred agent for coloring and/or lightening keratinic fibers is characterized in that it includes as (an) ethoxylated fatty alcohol (c) one or more compounds from the group of hexadecan-1-ol (hexadecyl alcohol, cetyl alcohol, palmityl alcohol) ethoxylated with 90 EO,
hexadecan-1-ol (hexadecyl alcohol, cetyl alcohol, palmityl alcohol) ethoxylated with 91 EO,
hexadecan-1-ol (hexadecyl alcohol, cetyl alcohol, palmityl alcohol) ethoxylated with 92 EO,
hexadecan-1-ol (hexadecyl alcohol, cetyl alcohol, palmityl alcohol) ethoxylated with 93 EO,
hexadecan-1-ol (hexadecyl alcohol, cetyl alcohol, palmityl alcohol) ethoxylated with 94 EO,
hexadecan-1-ol (hexadecyl alcohol, cetyl alcohol, palmityl alcohol) ethoxylated with 95 EO,
hexadecan-1-ol (hexadecyl alcohol, cetyl alcohol, palmityl alcohol) ethoxylated with 96 EO,
hexadecan-1-ol (hexadecyl alcohol, cetyl alcohol, palmityl alcohol) ethoxylated with 97 EO,
hexadecan-1-ol (hexadecyl alcohol, cetyl alcohol, palmityl alcohol) ethoxylated with 98 EO,
hexadecan-1-ol (hexadecyl alcohol, cetyl alcohol, palmityl alcohol) ethoxylated with 99 EO,
hexadecan-1-ol (hexadecyl alcohol, cetyl alcohol, palmityl alcohol) ethoxylated with 100 EO,
hexadecan-1-ol (hexadecyl alcohol, cetyl alcohol, palmityl alcohol) ethoxylated with 101 EO,
hexadecan-1-ol (hexadecyl alcohol, cetyl alcohol, palmityl alcohol) ethoxylated with 102 EO,
hexadecan-1-ol (hexadecyl alcohol, cetyl alcohol, palmityl alcohol) ethoxylated with 103 EO,
hexadecan-1-ol (hexadecyl alcohol, cetyl alcohol, palmityl alcohol) ethoxylated with 104 EO,
hexadecan-1-ol (hexadecyl alcohol, cetyl alcohol, palmityl alcohol) ethoxylated with 105 EO,
hexadecan-1-ol (hexadecyl alcohol, cetyl alcohol, palmityl alcohol) ethoxylated with 106 EO,
hexadecan-1-ol (hexadecyl alcohol, cetyl alcohol, palmityl alcohol) ethoxylated with 107 EO,
hexadecan-1-ol (hexadecyl alcohol, cetyl alcohol, palmityl alcohol) ethoxylated with 108 EO,
hexadecan-1-ol (hexadecyl alcohol, cetyl alcohol, palmityl alcohol) ethoxylated with 109 EO,
hexadecan-1-ol (hexadecyl alcohol, cetyl alcohol, palmityl alcohol) ethoxylated with 110 EO,
octadecan-1-ol (octadecyl alcohol, stearyl alcohol) ethoxylated with 90 EO,
octadecan-1-ol (octadecyl alcohol, stearyl alcohol) ethoxylated with 91 EO,
octadecan-1-ol (octadecyl alcohol, stearyl alcohol) ethoxylated with 92 EO,
octadecan-1-ol (octadecyl alcohol, stearyl alcohol) ethoxylated with 93 EO,
octadecan-1-ol (octadecyl alcohol, stearyl alcohol) ethoxylated with 94 EO,
octadecan-1-ol (octadecyl alcohol, stearyl alcohol) ethoxylated with 95 EO,
octadecan-1-ol (octadecyl alcohol, stearyl alcohol) ethoxylated with 96 EO,
octadecan-1-ol (octadecyl alcohol, stearyl alcohol) ethoxylated with 97 EO,
octadecan-1-ol (octadecyl alcohol, stearyl alcohol) ethoxylated with 98 EO,
octadecan-1-ol (octadecyl alcohol, stearyl alcohol) ethoxylated with 99 EO,
octadecan-1-ol (octadecyl alcohol, stearyl alcohol) ethoxylated with 100 EO,
octadecan-1-ol (octadecyl alcohol, stearyl alcohol) ethoxylated with 101 EO,
octadecan-1-ol (octadecyl alcohol, stearyl alcohol) ethoxylated with 102 EO,
octadecan-1-ol (octadecyl alcohol, stearyl alcohol) ethoxylated with 103 EO,
octadecan-1-ol (octadecyl alcohol, stearyl alcohol) ethoxylated with 104 EO,
octadecan-1-ol (octadecyl alcohol, stearyl alcohol) ethoxylated with 105 EO,
octadecan-1-ol (octadecyl alcohol, stearyl alcohol) ethoxylated with 106 EO,
octadecan-1-ol (octadecyl alcohol, stearyl alcohol) ethoxylated with 107 EO,
octadecan-1-ol (octadecyl alcohol, stearyl alcohol) ethoxylated with 108 EO,
octadecan-1-ol (octadecyl alcohol, stearyl alcohol) ethoxylated with 109 EO,
octadecan-1-ol (octadecyl alcohol, stearyl alcohol) ethoxylated with 110 EO.

The ammonia odor of the agents according to the present invention for coloring and/or lightening hair can in particular be masked completely during the entire utilization time period when the specially ethoxylated fatty alcohols (c) are employed in special quantity ranges.

In a further preferred embodiment, an agent for coloring and/or lightening keratinic fibers is therefore characterized in that it includes one or more ethoxylated fatty alcohols (c) having a degree of ethoxylation from 80 to 120 in a total quantity from 0.2 to 3.0 wt %, preferably from 0.4 to 2.4 wt %, more preferably from 0.6 to 1.8 wt %, and particularly preferably from 0.8 to 1.6 wt %, based on the weight of the agent.

As a fourth formulation constituent (d) essential to the invention, the agents according to the present invention include cetyl alcohol and stearyl alcohol in a total quantity of 4 to 8 wt.-%, based on the weight of the agent.

In cosmetic agents that included these two alcohols, it was possible to completely mask the ammonia over a particularly long period of time. In addition, it was possible with these agents to achieve coloring results with outstandingly good fastness properties, in particular good washing fastness and good gray coverage.

The fastness properties of the color results achievable with the agents according to the present invention can in particular be further optimized when the fatty alcohols (d) are also employed in special quantity ranges.

In a further particularly preferred embodiment, an agent for coloring and/or lightening keratinic fibers is therefore characterized in that the weight ratio of cetyl alcohol to stearyl alcohol lies within the range of 1.4 to 1.9.

As a fifth formulation constituent (e) essential to the invention, the agents according to the present invention include one or more ethoxylated fatty alcohols having a degree of ethoxylation of 30.

Suitable fatty alcohols having a degree of ethoxylation of 30 are dodecan-1-ol (dodecyl alcohol, lauryl alcohol) ethoxylated with 30 EO,
tetradecan-1-ol (tetradecyl alcohol, myristyl alcohol) ethoxylated with 30 EO, hexadecan-1-ol (hexadecyl alcohol, cetyl alcohol, palmityl alcohol) ethoxylated with 30 EO,
hexadecan-1-ol (hexadecyl alcohol, cetyl alcohol, palmityl alcohol) ethoxylated with 30 EO,
octadecan-1-ol (octadecyl alcohol, stearyl alcohol) ethoxylated with 30 EO,
(9Z)-octadec-9-en-1-ol (oleyl alcohol) ethoxylated with 30 EO,
(9E)-octadec-9-en-1-ol (elaidyl alcohol) ethoxylated with 30 EO,
(9Z,12Z)-octadeca-9,12-dien-1-ol (linoleyl alcohol) ethoxylated with 30 EO,
eicosan-1-ol (eicosyl alcohol, arachyl alcohol) ethoxylated with 30 EO,
docosan-1-ol (docosyl alcohol, behenyl alcohol) ethoxylated with 30 EO, and mixtures thereof.

Steareth-30 and/or ceteth-30 are especially preferred.

In a further preferred embodiment, an agent for coloring and/or lightening keratinic fibers is characterized in that it includes one or more ethoxylated fatty alcohols (e) having a degree of ethoxylation of 30 in a total quantity of 0.4 to 6.0 wt.-%, preferably 0.8 to 4.8 wt.-%, further preferred 1.2 to 3.6 wt.-% and especially preferred 1.6 to 3.2 wt.-%, based on the weight of the agent.

In a further preferred embodiment, an agent for coloring and/or lightening keratinic fibers is characterized in that it includes one or more ethoxylated fatty alcohols (e) having a degree of ethoxylation of 30, among them steareth-30 and/or ceteth-30, in a total quantity of 0.4 to 6.0 wt.-%, preferably 0.8 to 4.8 wt.-%, further preferred 1.2 to 3.6 wt.-% and especially preferred 1.6 to 3.2 wt.-%, based on the weight of the agent.

In a further particularly preferred embodiment, an agent according to the present invention is characterized in that it includes,
(a) 0.40 to 3.0 wt.-% ammonia,
(b) 0.40 to 13.0 wt.-% monoethanolamine,
(c) in a total quantity of 0.2 to 3.0 wt.-%, preferably 0.4 to 2.4 wt.-%, further preferred 0.6 to 1.8 wt.-% and especially preferred 0.8 to 1.6 wt.-%, of one or more ethoxylated fatty alcohols having a degree of ethoxylation from 80 to 120 that are selected from the group of:
octadecan-1-ol (octadecyl alcohol, stearyl alcohol) ethoxylated with 90 EO,
octadecan-1-ol (octadecyl alcohol, stearyl alcohol) ethoxylated with 91 EO,
octadecan-1-ol (octadecyl alcohol, stearyl alcohol) ethoxylated with 92 EO,
octadecan-1-ol (octadecyl alcohol, stearyl alcohol) ethoxylated with 93 EO,
octadecan-1-ol (octadecyl alcohol, stearyl alcohol) ethoxylated with 94 EO,
octadecan-1-ol (octadecyl alcohol, stearyl alcohol) ethoxylated with 95 EO,
octadecan-1-ol (octadecyl alcohol, stearyl alcohol) ethoxylated with 96 EO,
octadecan-1-ol (octadecyl alcohol, stearyl alcohol) ethoxylated with 97 EO,
octadecan-1-ol (octadecyl alcohol, stearyl alcohol) ethoxylated with 98 EO,
octadecan-1-ol (octadecyl alcohol, stearyl alcohol) ethoxylated with 99 EO,
octadecan-1-ol (octadecyl alcohol, stearyl alcohol) ethoxylated with 100 EO,
octadecan-1-ol (octadecyl alcohol, stearyl alcohol) ethoxylated with 101 EO,
octadecan-1-ol (octadecyl alcohol, stearyl alcohol) ethoxylated with 102 EO,
octadecan-1-ol (octadecyl alcohol, stearyl alcohol) ethoxylated with 103 EO,
octadecan-1-ol (octadecyl alcohol, stearyl alcohol) ethoxylated with 104 EO,
octadecan-1-ol (octadecyl alcohol, stearyl alcohol) ethoxylated with 105 EO,
octadecan-1-ol (octadecyl alcohol, stearyl alcohol) ethoxylated with 106 EO,
octadecan-1-ol (octadecyl alcohol, stearyl alcohol) ethoxylated with 107 EO,
octadecan-1-ol (octadecyl alcohol, stearyl alcohol) ethoxylated with 108 EO,
octadecan-1-ol (octadecyl alcohol, stearyl alcohol) ethoxylated with 109 EO,
octadecan-1-ol (octadecyl alcohol, stearyl alcohol) ethoxylated with 110 EO,
(d) cetyl alcohol and stearyl alcohol in a total quantity of 4 to 8 wt.-%, and
(e) in a total quantity of 0.4 to 6.0 wt.-%, preferably 0.8 to 4.8 wt.-%, further preferred 1.2 to 3.6 wt.-% and especially preferred 1.6 to 3.2 wt.-%, of one or more ethoxylated fatty alcohols having a degree of ethoxylation of 30 that are selected from the group of
dodecan-1-ol (dodecyl alcohol, lauryl alcohol) ethoxylated with 30 EO,
tetradecan-1-ol (tetradecyl alcohol, myristyl alcohol) ethoxylated with 30 EO,
hexadecan-1-ol (hexadecyl alcohol, cetyl alcohol, palmityl alcohol) ethoxylated with 30 EO,
hexadecan-1-ol (hexadecyl alcohol, cetyl alcohol, palmityl alcohol) ethoxylated with 30 EO,
octadecan-1-ol (octadecyl alcohol, stearyl alcohol) ethoxylated with 30 EO,
(9Z)-octadec-9-en-1-ol (oleyl alcohol) ethoxylated with 30 EO,
(9E)-octadec-9-en-1-ol (elaidyl alcohol) ethoxylated with 30 EO,
(9Z,12Z)-octadeca-9,12-dien-1-ol (linoleyl alcohol) ethoxylated with 30 EO, eicosan-1-ol (eicosyl alcohol, arachyl alcohol) ethoxylated with 30 EO,
docosan-1-ol (docosyl alcohol, behenyl alcohol) ethoxylated with 30 EO,
and mixtures thereof,
all quantity indications being based on the weight of the agent.

Preferred agents according to the present invention are characterized in that they include the ethoxylated fatty alcohols (e) with a degree of ethoxylation of 30 and the ethoxylated fatty alcohols (c) with a degree of ethoxylation from 80 to 120 in a weight ratio (e)/(c) of at least 1:1, preferably in a weight ratio (e)/(c) of at least 1.5:1, and especially preferred in a weight ratio (e)/(c) of at least 2:1, in each case referring to the total quantity of all ethoxylated fatty alcohols (e) and to the total quantity of all ethoxylated fatty alcohols (c) that are included in the agent.

Because the agents according to the present invention are agents for oxidative coloring of hair, they therefore additionally include oxidation dye precursors in order to form the dyes.

Categorized among the oxidation dye precursors are oxidation dye precursors of the developer type and of the coupler type. Particularly suitable oxidation dye precursors of the developer type are selected from at least one compound from the group of p-phenylenediamine, p-toluylenediamine, 2-(2-hydroxyethyl)-p-phenylenediamine, 2-(1,2- dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,1-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl) phenol, 4-amino-2-(diethylaminomethyl) phenol, 4,5-diamino-1-(2-hydroxyethyl) pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, and physiologically acceptable salts thereof.

Particularly suitable oxidation dye precursors of the coupler type are selected from the group of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of said compounds or physiologically acceptable salts thereof.

In a preferred embodiment, the agents according to the present invention additionally include one or more oxidation dye precursors in a total quantity from 0.01 to 8.0 wt %, preferably from 0.1 to 7.0 wt %, more preferably from 1.0 to 6.0 wt %, and very particularly preferably from 2.0 to 5.0 wt %, based on the weight of the agent.

In a further preferred embodiment, the agents according to the present invention additionally include at least one further substantive dye. Substantive dyes can be subdivided into anionic, cationic, and nonionic substantive dyes. The substantive dyes are preferably selected from nitrophenylenediamines, nitroaminophenols, azo dyes, anthraquinones, triarylmethane dyes, or indophenols, and physiologically acceptable salts thereof. The additional substantive dyes are respectively employed preferably in a proportion from 0.001 to 4 wt %, based on the weight of the agent.

Preferred anionic substantive dyes are the compounds known by the international designations or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue, and tetrabromophenol blue.

Preferred cationic substantive dyes are cationic triphenylmethane dyes such as, for example, Basic Blue 7, Basic Blue 26, Basic Violet 2, and Basic Violet 14, aromatic systems that are substituted with a quaternary nitrogen group, for example Basic Yellow 57, Basic Red 76, Basic Blue 99, Basic Brown 16, and Basic Brown 17, cationic anthraquinone dues such as HC Blue 16 (Bluequat B), as well as substantive dyes which include a heterocycle that comprises at least one quaternary nitrogen atom, in particular Basic Yellow 87, Basic Orange 31, and Basic Red 51. The cationic substantive dyes that are marketed under the Arianor® trademark are likewise preferred cationic substantive dyes according to the present invention.

Nonionic nitro and quinone dyes, and neutral azo dyes, are particularly suitable as nonionic substantive dyes. Preferred nonionic substantive dyes are the compounds known by the international designations or commercial names HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropylamino]-3-nitrophenol, 4-nitro-o-phenylenediamine, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

Formation of the dyes in oxidative coloring agents occurs only under the influence of an oxidizing agent; hydrogen peroxide is usually used for this. In a preferred embodiment, hydrogen peroxide is used as an aqueous solution. According to the present invention, it is preferred that the agent according to the present invention (IA) and the accompanying oxidizing agent preparation (OA) are optimized for a weight-based mixing ratio (IA)/(OA) in the range of 0.33 to 3, preferably 0.5 to 2 and especially preferred 1 to 1. Oxidizing agent preparations preferably used according to the present invention are characterized in that they include, based on their weight, water and 1.0 to 23.0 wt %, more preferably 2.5 to 21.0 wt %, particularly preferably 4.0 to 20.0 wt %, and very particularly preferably 5.0 to 18.0 wt % hydrogen peroxide (calculated as 100-percent $H_2O_2$).

Further preferably used oxidizing agent preparations are characterized in that they include one or more fatty alcohols from the group lauryl alcohol, myristyl alcohol, cetyl alcohol, stearyl alcohol, arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), in a total quantity of 0.01 to 3 wt.-%, preferably 0.1 to 2 wt.-%, based on the weight of the oxidizing agent preparation.

Further preferably used oxidizing agent preparations are characterized in that they include at least one surfactant in a total quantity of 0.01 to 3 wt.-%, preferably 0.1 to 2 wt.-%, especially preferred 0.2 to 0.5 wt.-%, based on the weight of the oxidizing agent preparation.

Further preferably used oxidizing agent preparations are characterized in that they include at least one oil in a total quantity of 0.01 to 3 wt.-%, preferably 0.1 to 2 wt.-%, especially preferred 0.2 to 0.5 wt.-%, based on the weight of the oxidizing agent preparation.

Especially preferred used oxidizing agent preparations are characterized in that they include, based on their weight, 80 to 95 wt.-% water, 1.0 to 23.0 wt %, more preferably 2.5 to 21.0 wt %, particularly preferably 4.0 to 20.0 wt %, and very particularly preferably 5.0 to 18.0 wt % hydrogen peroxide (calculated as 100-percent $H_2O_2$), one or more fatty alcohols from the group lauryl alcohol, myristyl alcohol, cetyl alcohol, stearyl alcohol, arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), in a total quantity of 0.01 to 3 wt.-%, preferably 0.1 to 2 wt.-%, and at least one surfactant in a total quantity of 0.01 to 3 wt.-%, preferably 0.1 to 2 wt.-%, especially preferred 0.2 to 0.5 wt.-%, and optionally at least one oil in a total quantity of 0.01 to 3 wt.-%, preferably 0.1 to 2 wt.-%, especially preferred 0.2 to 0.5 wt.-%.

It has proven to be advantageous if the oxidizing agent preparations according to the present invention additionally include at least one stabilizer or complexing agent in order to stabilize the hydrogen peroxide. Particularly preferred stabilizers are, in particular, EDTA and EDDS, and phosphonates, in particular 1-hydroxyethane-1,1-diphosphonate (HEDP) and/or ethylenediaminetetramethylenephosphonate (EDTMP) and/or diethylenetriaminepentamethylenephosphonate (DTPMP) or sodium salts thereof.

Furthermore, the agents according to the present invention can additionally include polymers and/or thickeners. Cationic, anionic, and/or zwitterionic polymers can be used as polymers. Examples of suitable anionic polymers are obtainable commercially, for example, under the trade names Carbopol® or Rheothik® 11-80. The polymers marketed under the INCI name Acrylates Copolymers are also suitable anionic polymers. A preferred commercial product is, for example, Aculyn® 33 of the Rohm & Haas company. Further preferred anionic polymers are marketed by the Rohm & Haas company under the trade name Aculyn® 22 and by the National Starch company under the trade names Structure® 2001 and Structure® 3001.

Suitable additionally usable cationic polymers are, for example, Polyquaternium-24 (commercial product e.g. Quatrisoft® LM 200), Copolymer 845 (manufacturer: ISP), Gaffix® VC 713 (manufacturer: ISP), Gafquat® ASCP 1011, Gafquat® HS 110, Luviquat® 8155, and Luviquat® MS 370.

As naturally occurring thickening agents, nonionic guar gums such as, for example, both modified (e.g. Jaguar® HP8, Jaguar® HP60, Jaguar® HP120, Jaguar® DC 293, and Jaguar® HP105) and unmodified guar gums (e.g. Jaguar® C) can be used. Further suitable thickening agents are scleroglucan gums or xanthan gums, gums, gum arabic, ghatti gum, karaya gum, tragacanth gum, carrageenan gum, agar-agar, locust bean flour, pectins, alginates, starch fractions and derivatives such as amylose, amylopectin, and dextrins, cellulose derivatives, e.g. methyl cellulose, carboxyalkyl celluloses, and hydroxyalkyl celluloses.

Further anionic, cationic, or amphoteric surfactants can likewise be included in the agents according to the present invention. Preferred anionic surfactants are alkyl sulfates, alkyl ether sulfates, and ethercarboxylic acids having 10 to 18 carbon atoms in the alkyl group and up to 12 glycol ether groups in the molecule. Particularly preferred amphoteric surfactants are N-cocalkylaminopropionate, cocacylaminoethylaminopropionate, and $C_{12}$ to $C_{18}$ acylsarcosine.

Preferred additionally included cationic surfactants are, for example, ammonium halides, in particular chlorides and bromides, such as alkyltrimethylammonium chlorides, dialkyldimethylammonium chlorides, and trialkylmethylammonium chlorides, for example cetyltrimethylammonium chloride, stearyltrimethylammonium chloride, distearyldimethylammonium chloride, lauryldimethylammonium chloride, lauryldimethylbenzylammonium chloride, and tricetylmethylammonium chloride, as well as the imidazolium compounds known by the INCI names Quaternium-27 and Quaternium-83.

Coloring and lightening processes on keratin fibers usually proceed in an alkaline environment. In order to minimize stress on the keratin fibers and also on the skin, however, it is not desirable to establish too high a pH. It is therefore preferred if the pH of the agent according to the present invention is between 6 and 12, in particularly between 7 and 10.5. The pH values for purposes of the present invention are pH values that were measured at a temperature of 22° C.

The agents according to the present invention are agents for oxidative coloring and/or lightening of hair. In the ready-to-use agent, the oxidation dye precursors react with the oxidizing agent, accompanied by formation of the actual dyes. The agents according to the present invention are therefore commercialized as multi-component kits, in most cases as two-component kits. The first component includes the oxidation dye precursors and the alkalizing agent (preparation A), which is mixed shortly before utilization with a second component including the oxidizing agent (preparation B). The two components are usually mixed with one another at a weight ratio from 1:3 to 3:1, preferably 1:2 to 2:1, especially preferred 1:1. This mixture of the component including color cream/alkalizing agent (preparation A) and the component including oxidizing agent (preparation B) is referred to as the "utilization mixture" or the "ready-to-use agent." All quantity indications with reference to the "ready-to-use agent" refer to the ready-to-use mixture of the agent according to the present invention, including dyestuff/alkalizing agent, and the component including oxidizing agent. All quantity indications with reference to the "agent" refer to the agent according to the present invention, including dyestuff/alkalizing agent.

A further subject of the present invention is therefore a ready-to-use agent for coloring and/or lightening keratinic fibers, which is characterized in that it is produced immediately before utilization by mixing preparations (A) and (B) in a weight-based mixing ratio (A)/(B) in the range of 0.33 to 3, preferably 0.5-2, especially preferred 1:1, wherein
    preparation (A) is an agent of the first subject of the invention,
    preparation (B) is an agent that includes, based on the weight of preparation (B), 80 to 95 wt.-% water, 1.0 to 23.0 wt %, more preferably 2.5 to 21.0 wt %, particularly preferably 4.0 to 20.0 wt %, and very particularly preferably 5.0 to 18.0 wt % hydrogen peroxide (calculated as 100-percent $H_2O_2$), and optionally one or more fatty alcohols from the group lauryl alcohol, myristyl alcohol, cetyl alcohol, stearyl alcohol, arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), in a total quantity of 0.01 to 3 wt.-%, preferably 0.1 to 2 wt.-%, further optionally at least one surfactant in a total quantity of 0.01 to 3 wt.-%, preferably 0.1 to 2 wt.-%, especially preferred 0.2 to 0.5 wt.-%, and further optionally at least one oil in a total quantity of 0.01 to 3 wt.-%, preferably 0.1 to 2 wt.-%, especially preferred 0.2 to 0.5 wt.-%.

A further subject of the present invention is a method for coloring and/or lightening keratinic fibers which is characterized in that if desired, a pretreatment agent PRE is applied onto the fibers, then a coloring and/or lightening agent (A), corresponding to the agent according to any of claims 1 to 11, is applied to the fibers, a further agent (B) being added if desired to the agent (A) before utilization, wherein preferably (A) and (B) are present in a weight-based mixing ratio (A)/(B) in the range of 0.33 to 3, preferably 0.5-2, especially preferred 1:1, and wherein the agent (B) preferably includes, based on the weight of preparation (B), 80 to 95 wt.-% water, 1.0 to 23.0 wt %, more preferably 2.5 to 21.0 wt %, particularly preferably 4.0 to 20.0 wt %, and very particularly preferably 5.0 to 18.0 wt % hydrogen peroxide (calculated as 100-percent $H_2O_2$), and optionally one or more fatty alcohols from the group lauryl alcohol, myristyl alcohol, cetyl alcohol, stearyl alcohol, arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), in a total quantity of 0.01 to 3 wt.-%, preferably 0.1 to 2 wt.-%, further optionally at least one surfactant in a total quantity of 0.01 to 3 wt.-%, preferably 0.1 to 2 wt.-%, especially preferred 0.2 to 0.5 wt.-%, and further optionally at least one oil in a total quantity of 0.01 to 3 wt.-%, preferably 0.1 to 2 wt.-%, especially preferred 0.2 to 0.5 wt.-%, the fibers are rinsed after a time from 5 to 30 minutes, and after treatment, optionally a post-treatment agent "POST" is applied onto the fibers and is rinsed off again after a contact time from 0.5 to 25 minutes.

The statements made about the agents according to the present invention apply mutatis mutandis with regard to further preferred embodiments of the kits, methods and uses according to the present invention.

EXAMPLES

The following formulation was produced:

| Formulation constituents (color cream) | E1 (wt %) |
| --- | --- |
| Cetyl alcohol | 3.60 |
| Stearyl Alcohol | 2.0 |
| Eumulgin B 3 (INCI: Ceteareth-30) | 1.2 |
| Brij S 100 PA (Stearyl alcohol ethoxylated (100 EO)) | 0.6 |
| Cutina GMS (INCI: Glyceryl Stearate) | 0.6 |
| Propylene glycol | 6.0 |
| p-Toluylenediamine sulfate | 0.50 |
| Resorcinol | 0.06 |
| 2-Amino-3-hydroxypyridine | 0.06 |
| 4-Chlorresorcinol | 0.08 |
| 2-Methylresorcinol | 0.08 |
| 2-amino-6-chloro-4-nitrophenol | 0.06 |
| Ethylenediaminetetraacetic acid, tetrasodium salt | 0.20 |
| Sodium sulfite (anhydrous) | 0.30 |
| Vitamin C | 0.05 |

-continued

| Formulation constituents (color cream) | E1 (wt %) |
| --- | --- |
| Product W 37194 ((N,N,N-trimethyl-3-[(1-oxo-2-propenyl)amino]-1-propanaminium chloride, polymer with sodium 2-propenoate) (INCI: Acrylamidopropyltrimonium Chloride/Acrylate Copolymer) 20-wt % aqueous solution | 4.00 |
| Monoethanolamine | 2.00 |
| Ammonia (25-wt % aqueous solution) | 7.00 |
| Ammonium sulfate | 0.90 |
| Perfume | 0.40 |
| Water | to 100 |

E1 is a formulation according to the present invention. The color cream was mixed at a 1:1 ratio with the following oxidizing agent formulation (OX1).

| Formulation constituents | OX1 (wt %) |
| --- | --- |
| Phosphoric acid, 85% | 0.04 |
| Hydrogen peroxide (50%, aqueous solution) | 12.00 |
| Emulgade F (INCI: Cetearyl Alcohol, PEG-40, Castor Oil, Sodium Cetearyl Sulfate) | 2.10 |
| Sodium benzoate | 0.04 |
| Disodium pyrophosphate | 0.30 |
| Ethylenediaminetetraacetate, disodium salt | 0.15 |
| Water | to 100 |

The utilization mixture produced in this manner was applied with an Aplicette onto hair strands (yak belly hair) and left there for a time period from 30 minutes. The utilization mixture was then rinsed out with a shampoo and dried. A caramel blonde color was obtained.

2. Determining Ammonia Odor During Utilization

The utilization mixture previously produced (E1+OX1) was applied onto the head of a test subject. During the utilization time period, the ammonia odor was evaluated in each case by five trained persons at various points in time (directly after application at 0 min, after 10 min, after 20 min, and after 30 min) The evaluation was performed blind, meaning that the persons who performed the evaluation did not know which formulation they were evaluating at the time. The average was calculated from the individual evaluations.

The ammonia odor was evaluated on a scale from 0 (virtually no odor perceptible) to 10 (very strong ammonia odor).

TABLE 4

Ammonia odor during utilization (utilization mixture)

| | after 0 min | after 10 min | after 20 min | after 30 min |
| --- | --- | --- | --- | --- |
| E1 + OX1 | 0-1 | 0-1 | 0-1 | 0-1 |

It is evident that the ammonia odor in the context of utilization of the formulation according to the present invention, both directly after application of the formulation and after a period of 10 minutes, 20 minutes, and 30, was perceived as appreciably reduced.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An agent for coloring and/or lightening keratinic fibers, in particular human hair, including:
    (a) ammonia in a quantity of 0.40 to 3.0 wt. % based on the weight of the agent,
    (b) one or more alkanolamines from the group of monoethanolamine, 2-amino-2-methylpropanol, and triethanolamine,
    (c) one or more ethoxylated fatty alcohols having a degree of ethoxylation from 80 to 120,
    (d) cetyl alcohol and stearyl alcohol in a total quantity of 4 to 8 wt-%, based on the weight of the agent, and
    (e) one or more ethoxylated fatty alcohols having a degree of ethoxylation of 30 and selected from the group consisting of
        dodecan-1-ol (dodecyl alcohol, lauryl alcohol) ethoxylated with 30 EO,
        tetradecan-1-ol (tetradecyl alcohol, myristyl alcohol) ethoxylated with 30 EO,
        hexadecan-1-ol (hexadecyl alcohol, cetyl alcohol, palmityl alcohol) ethoxylated with 30 EO,
        hexadecan-1-ol (hexadecyl alcohol, cetyl alcohol, palmityl alcohol) ethoxylated with 30 EO,
        octadecan-1-ol (octadecyl alcohol, stearyl alcohol) ethoxylated with 30 EO,
        (9Z)-octadec-9-en-1-ol (oleyl alcohol) ethoxylated with 30 EO,
        (9E)-octadec-9-en-1-ol (elaidyl alcohol) ethoxylated with 30 EO,
        (9Z,12Z)-octadeca-9,12-dien-1-ol (linoleyl alcohol) ethoxylated with 30 EO,
        eicosan-1-ol (eicosyl alcohol, arachyl alcohol) ethoxylated with 30 EO,
        docosan-1-ol (docosyl alcohol, behenyl alcohol) ethoxylated with 30 EO.

2. The agent according to claim 1, characterized in that the weight ratio of cetyl alcohol to stearyl alcohol lies in the range of 1.4 to 1.9.

3. The agent according to claim 1, characterized in that it includes one or more alkanolamines (b) from the group of monoethanolamine, 2-amino-2-methylpropanol, and triethanolamine in a total quantity from 0.4 to 13 wt % based on the weight of the agent.

4. The agent according to claim 1, characterized in that it includes as (an) ethoxylated fatty alcohol(s) (c) having a degree of ethoxylation from 80 to 120 one or more compounds of formula (I)

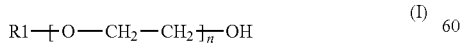

$$R1\!-\!\!+\!\!O\!-\!CH_2\!-\!CH_2\!\!+\!\!_n\!-\!OH \qquad (I)$$

in which R1 denotes a saturated or unsaturated, unbranched or branched $C_8$ to $C_{24}$ alkyl group, and n denotes an integer from 80 to 120.

5. The agent according to claim 1, characterized in that it includes one or more ethoxylated fatty alcohols (c) having a degree of ethoxylation from 80 to 120 in a total quantity from 0.2 to 3.0 wt % based on the weight of the agent.

6. The agent according to claim 1, characterized in that it includes one or more ethoxylated fatty alcohols (e) having a degree of ethoxylation of 30 in a total quantity from 0.4 to 6.0 wt % based on the weight of the agent.

7. The agent according to claim 1, characterized in that it includes the ethoxylated fatty alcohols (e) with a degree of ethoxylation of 30 and the ethoxylated fatty alcohols (c) with a degree of ethoxylation from 80 to 120 in a weight ratio (e)/(c) of at least 1:1 referring to the total quantity of all ethoxylated fatty alcohols (e) and to the total quantity of all ethoxylated fatty alcohols (c) that are included in the agent.

8. The agent according to claim 1, characterized in that it includes
    (a) 0.40 to 3.0 wt.-% ammonia,
    (b) 0.40 to 13.0 wt.-% monoethanolamine,
    (c) one or more ethoxylated fatty alcohols having a degree of ethoxylation from 80 to 120 in a total quantity of 0.2 to 3.0 wt.-%,
    (d) cetyl alcohol and stearyl alcohol in a total quantity of 4 to 8 wt-%, and
    (e) one or more ethoxylated fatty alcohols having a degree of ethoxylation 30 in a total quantity of 0.4 to 6.0 wt.-%,
all quantity indications being based on the weight of the agent.

9. The agent according to claim 1, characterized in that it includes
    (a) 0.40 to 3.0 wt.-% ammonia,
    (b) 0.40 to 13.0 wt.-% monoethanolamine,
    (c) one or more ethoxylated fatty alcohols having a degree of ethoxylation from 80 to 120 in a total quantity of 0.2 to 3.0 wt.-%, among them steareth-100,
    (d) cetyl alcohol and stearyl alcohol in a total quantity of 4 to 8 wt-%, and
    (e) one or more ethoxylated fatty alcohols having a degree of ethoxylation 30 in a total quantity of 0.4 to 6.0 wt.-%, among them steareth-30 and/or ceteth-30,
all quantity indications being based on the weight of the agent.

10. A ready-to-use agent for coloring and/or lightening keratinic fibers, characterized in that it is produced immediately before utilization by mixing preparations (A) and (B) in a weight-based mixing ratio (A)/(B) in the range of 0.33 to 3, wherein
    preparation (A) is an agent according to claim 1,
    preparation (B) is an agent that includes, based on the weight of preparation (B), 80 to 95 wt.-% water, 1.0 to 23.0 wt % hydrogen peroxide calculated as 100-percent $H_2O_2$, and optionally one or more fatty alcohols selected from the group consisting of lauryl alcohol, myristyl alcohol, cetyl alcohol, stearyl alcohol, arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), in a total quantity of 0.01 to 3 wt.-%, further optionally at least one surfactant in a total quantity of 0.01 to 3 wt.-%, and further optionally at least one oil in a total quantity of 0.01 to 3 wt.-%.

11. A method for coloring and/or lightening keratinic fibers, which comprises:
    optionally, applying a pretreatment agent PRE onto the fibers, then applying a coloring and/or lightening agent (A), corresponding to the agent according to claim 1, to the fibers, a further agent (B) being optionally added to the agent (A) before utilization, wherein (A) and (B), when (B) is added, are present in a weight-based mixing ratio (A)/(B) in the range of 0.33 to 3, and wherein the agent (B) includes, based on the weight of preparation (B) when added, 80 to 95 wt.-% water, 1.0 to 23.0 wt % hydrogen peroxide calculated as 100-percent $H_2O_2$, and optionally one or more fatty alcohols selected from the group consisting of lauryl alcohol, myristyl alcohol, cetyl alcohol, stearyl alcohol, arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), behenyl alcohol (docosan-1-ol), erucyl alcohol ((13Z)-docos-13-en-1-ol), and brassidyl alcohol ((13E)-docosen-1-ol), in a total quantity of 0.01 to 3 wt.-% further optionally at least one surfactant in a total quantity of 0.01 to 3 wt.-%, and further optionally at least one oil in a total quantity of 0.01 to 3 wt.-%, rinsing the fibers after a time from 5 to 30 minutes, and after treatment, optionally applying a post-treatment agent "POST" onto the fibers and is rinsed off again after a contact time from 0.5 to 25 minutes.

\* \* \* \* \*